(12) United States Patent
Chen et al.

(10) Patent No.: US 10,772,628 B2
(45) Date of Patent: Sep. 15, 2020

(54) STAPLE CARTRIDGE ASSEMBLY AND MEDICAL STAPLER USING THE STAPLE CARTRIDGE ASSEMBLY

(71) Applicant: TOUCHSTONE INTERNATIONAL MEDICAL SCIENCE CO., LTD., Suzhou (CN)

(72) Inventors: Wangdong Chen, Suzhou (CN); Tuo Shu, Suzhou (CN); Yanping Ye, Suzhou (CN); Hui Gao, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 461 days.

(21) Appl. No.: 15/540,959

(22) PCT Filed: Dec. 22, 2015

(86) PCT No.: PCT/CN2015/098180
§ 371 (c)(1),
(2) Date: Jun. 29, 2017

(87) PCT Pub. No.: WO2016/107449
PCT Pub. Date: Jul. 7, 2016

(65) Prior Publication Data
US 2017/0348003 A1 Dec. 7, 2017

(30) Foreign Application Priority Data
Dec. 30, 2014 (CN) .......................... 2014 1 0841670

(51) Int. Cl.
*A61B 17/072* (2006.01)
*A61B 17/00* (2006.01)
*A61B 90/00* (2016.01)

(52) U.S. Cl.
CPC ...... *A61B 17/07207* (2013.01); *A61B 17/072* (2013.01); *A61B 2017/0046* (2013.01);
(Continued)

(58) Field of Classification Search
CPC .......... A61B 17/00491; A61B 17/0644; A61B 17/068; A61B 17/07207; A61B 17/105;
(Continued)

(56) References Cited

U.S. PATENT DOCUMENTS 9,585,657 B2 * 3/2017 Shelton, IV ..... A61B 17/07207
10,390,823 B2 * 8/2019 Shelton, IV
(Continued)

FOREIGN PATENT DOCUMENTS

| CN | 101966093 A | 2/2011 |
|----|-------------|--------|
| CN | 103654898 A | 3/2014 |

(Continued)

OTHER PUBLICATIONS

International Search report, dated Mar. 22, 2016, for international Application No. PCT/CN2015/098180, 4 pages.

*Primary Examiner* — Thanh K Truong
*Assistant Examiner* — Thomas M Wittenschlaeger
(74) *Attorney, Agent, or Firm* — Seed IP Law Group LLP

(57) ABSTRACT

A staple cartridge assembly comprises a connector, a cutter push rod and an elastic sheet, the elastic sheet having a first through groove and the cutter push rod being formed by laminating multiple sheets, wherein when the staple cartridge assembly is in an original status or a closed status, part of the cutter push rod is located in the first through groove, and the first through groove restricts detaching of the multiple sheets in a laminating direction of the multiple sheets; in a firing process of the staple cartridge assembly, the cutter push rod moves towards a distal end of the staple cartridge assembly to press the elastic sheet, such that the (Continued)

elastic sheet deforms and the cutter push rod is gradually detached from the first through groove; after the firing of the staple cartridge assembly is finished, the cutter push rod is detached from the first through groove.

8 Claims, 8 Drawing Sheets

(52) U.S. Cl.
CPC ............ *A61B 2017/00477* (2013.01); *A61B 2017/00862* (2013.01); *A61B 2017/07257* (2013.01); *A61B 2017/07271* (2013.01); *A61B 2017/07278* (2013.01); *A61B 2017/07285* (2013.01); *A61B 2090/034* (2016.02)

(58) Field of Classification Search
CPC .......... A61B 2017/07228; A61B 2017/07235; A61B 2017/0725; A61B 2017/07257; A61B 2017/07271; A61B 2017/07278; A61B 2017/0046; A61B 2017/00477; A61B 2017/00862; A61B 2017/07285; A61B 2090/034
See application file for complete search history.

(56) References Cited

U.S. PATENT DOCUMENTS

| | | | | |
|---|---|---|---|---|
| 2004/0232201 | A1* | 11/2004 | Wenchell | A61B 17/07207 227/176.1 |
| 2009/0114701 | A1 | 5/2009 | Zemlok et al. | |
| 2009/0206130 | A1* | 8/2009 | Hall | A61B 17/07207 227/175.2 |
| 2009/0206131 | A1* | 8/2009 | Weisenburgh, II | A61B 17/07207 227/175.2 |
| 2012/0286021 | A1* | 11/2012 | Kostrzewski | A61B 17/07207 227/175.2 |
| 2013/0075451 | A1* | 3/2013 | Balek | A61B 17/00491 227/180.1 |
| 2013/0214030 | A1 | 8/2013 | Aronhalt et al. | |
| 2015/0053748 | A1* | 2/2015 | Yates | A61B 34/74 227/180.1 |
| 2015/0265275 | A1 | 9/2015 | Chen et al. | |
| 2015/0374363 | A1* | 12/2015 | Laurent, IV | A61B 17/068 227/175.3 |
| 2015/0374373 | A1* | 12/2015 | Rector | A61B 17/0644 606/219 |
| 2016/0058444 | A1* | 3/2016 | Shelton, IV | A61B 17/07207 227/177.1 |
| 2016/0058447 | A1* | 3/2016 | Posada | A61B 17/105 227/177.1 |
| 2018/0042611 | A1* | 2/2018 | Swayze | A61B 18/1445 |

FOREIGN PATENT DOCUMENTS

| | | |
|---|---|---|
| CN | 104434250 A | 3/2015 |
| CN | 204379338 U | 6/2015 |

* cited by examiner

STAPLE CARTRIDGE ASSEMBLY AND MEDICAL STAPLER USING THE STAPLE CARTRIDGE ASSEMBLY

This application claims the priority of the Chinese patent application No. 201410841670.6, filed on Dec. 31, 2014 and titled "staple cartridge assembly and medical stapler using the staple cartridge assembly", which is incorporated herein by reference in its entirety.

TECHNICAL FIELD

The present invention is related to the technical field of medical instruments, and more particularly, to a staple cartridge assembly and a medical stapler using the staple cartridge assembly.

BACKGROUND

A medical stapler is a common medical instrument when performing surgeries to physiological tissues such as intestinal tissues. It is a medical device replacing manual suturing. With development of modern technologies and improvement of manufacturing techniques, current medical staplers are reliable in quality, convenient in use and appropriate in tightness and tension of suturing. They have the advantages of quick suturing, simple operation and less side effects and surgical complications. Sometimes, they can cut tumor tissues which could not be removed in past surgeries, so they are praised highly by foreign and domestic surgeons. The difference in performance of such instruments plays a crucially important role in the surgical effects.

At present, a cutter push rod of a medical stapler may be formed by multiple thin sheets, each sheet has a thickness of about 0.25 mm. As the sheets are very thin and elastic, the cutter push rod formed by such multiple sheets can be deformed under external forces. In practice, during a firing process of a medical stapler and a bending process of a cutter push rod, the multiple sheets are applied with a great external force, such that the multiple sheets can easily deform or detach from one another in their laminating direction, whereby, result in the firing of the medical stapler may not be sufficient.

SUMMARY

The objectives of the present invention are to provide a staple cartridge assembly and a medical stapler using the staple cartridge assembly.

To realize one of the above objectives, an embodiment of the present invention provides a staple cartridge assembly. The staple cartridge assembly comprises a connector, a cutter push rod and an elastic sheet, the elastic sheet having a first through groove and the cutter push rod being formed by laminating multiple sheets, wherein when the staple cartridge assembly is in an original status or a closed status, part of the cutter push rod is located in the first through groove, and the first through groove restricts detaching of the multiple sheets in a laminating direction of the multiple sheets; in a firing process of the staple cartridge assembly, the cutter push rod moves towards a distal end of the staple cartridge assembly to press the elastic sheet, such that the elastic sheet deforms and the cutter push rod is gradually detached from the first through groove; after the firing of the staple cartridge assembly is finished, the cutter push rod is detached from the first through groove.

As an improvement of the embodiment of the present invention, the cutter push rod includes a first end surface formed by laminating the multiple sheets and a second end surface away from the first end surface; when the staple cartridge assembly is in the original status or the closed status, a distance from the highest point of the elastic sheet to the first end surface is greater than that from the highest point to the second end surface; in the firing process of the staple cartridge assembly, the highest point gradually departs from the second end surface and gradually approaches the first end surface; after the firing of the staple cartridge assembly is finished, the elastic sheet is detached from the cutter push rod.

As another improvement of the embodiment of the present invention, the elastic sheet includes a first end and a second end that are movably connected to the connector; the first end is located at a distal end of the second end; during the firing process of the staple cartridge assembly, the first end moves towards the distal end of the staple cartridge assembly, and the second end moves towards the proximal end thereof.

As yet another improvement of the embodiment of the present invention, the elastic sheet includes a first end movably connected to the connector and a second end fixedly connected to the connector; the first end is located at a distal end of the second end; during the firing process of the staple cartridge assembly, the first end moves towards the distal end of the staple cartridge assembly.

As yet another improvement of the embodiment of the present invention, the staple cartridge assembly further includes a limiting member; a second through groove is provided between the first end and the first through groove, and is movably connected to the connector via the limiting member; when the staple cartridge assembly is in the original status or the closed status, the second through groove is stationary relative to the limiting member; during the firing process of the staple cartridge assembly, the limiting member can slide in the second through groove, and the second through groove moves towards the distal end of the staple cartridge assembly relative to the limiting member.

As yet another improvement of the embodiment of the present invention, the limiting member is a limiting nail fixedly connected to the connector.

As yet another improvement of the embodiment of the present invention, the cutter push rod includes a cutter push rod main body and a tail end; the tail end is located at the proximal end of the cutter push rod main body; an abutting portion is provided between the proximal end of the first through groove and the second end; when the cutter push rod moves towards the distal end of the staple cartridge assembly, the tail end presses the abutting portion to deform the elastic sheet.

As yet another improvement of the embodiment of the present invention, the elastic sheet is located at a midway between the proximal and distal ends of the connector.

To realize one of the above objectives, an embodiment of the present invention provides a medical stapler including the staple cartridge assembly of any of the above technical solutions.

As an improvement of the embodiment of the present invention, the medical stapler further includes a firing rod which abuts against the elastic sheet after the firing of the medical stapler is finished.

Compared with the prior art, the present invention may produce the following advantageous effects. In the present invention, by limiting the multiple sheets using the first through groove in the elastic sheet, the multiple sheets do not detach from one another in their laminating direction; the cutter push rod can smoothly move towards the distal or proximal end of the medical stapler through the deformation of the elastic sheet, and blocking of the cutter push rod by the elastic sheet is avoided.

DETAILED DESCRIPTION

The followings will describe the present invention in detail with reference to the embodiments shown in the figures. However, these embodiments do not limit the present invention. Modifications to the structure, method or function based on these embodiments made by those skilled in the art all also included in the protection scope of the present invention.

The terms expressing the positions and directions used in the present invention use the instrument operator as the reference object. The end close to the operator is the proximal end, and the end far away from the operator is the distal end.

In the embodiments of the present invention, specific illustrations are made by taking an endoscopic surgical cutting stapler as an example. But it should be noted that other forms of staplers may be alternatively applied within the scope and spirit of the following embodiments.

Figure 1:
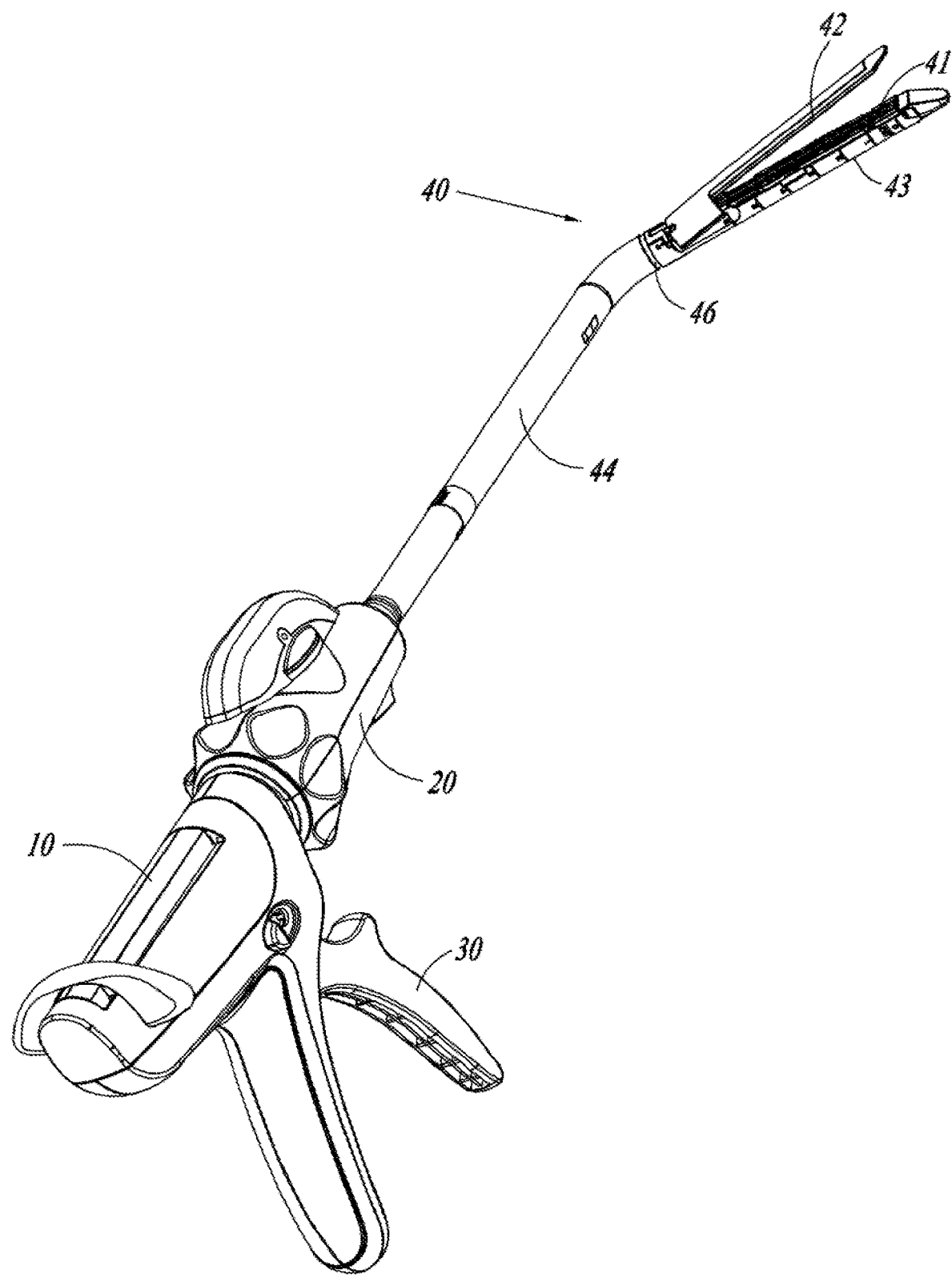
FIG. 1 is a schematic structural view of a medical stapler according an embodiment of the present invention.
Figure 2:
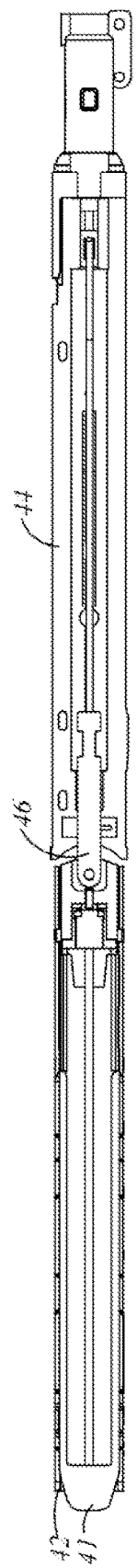
FIG. 2 is a plan view of a stapler cartridge assembly according an embodiment of the present invention.
Figure 3:
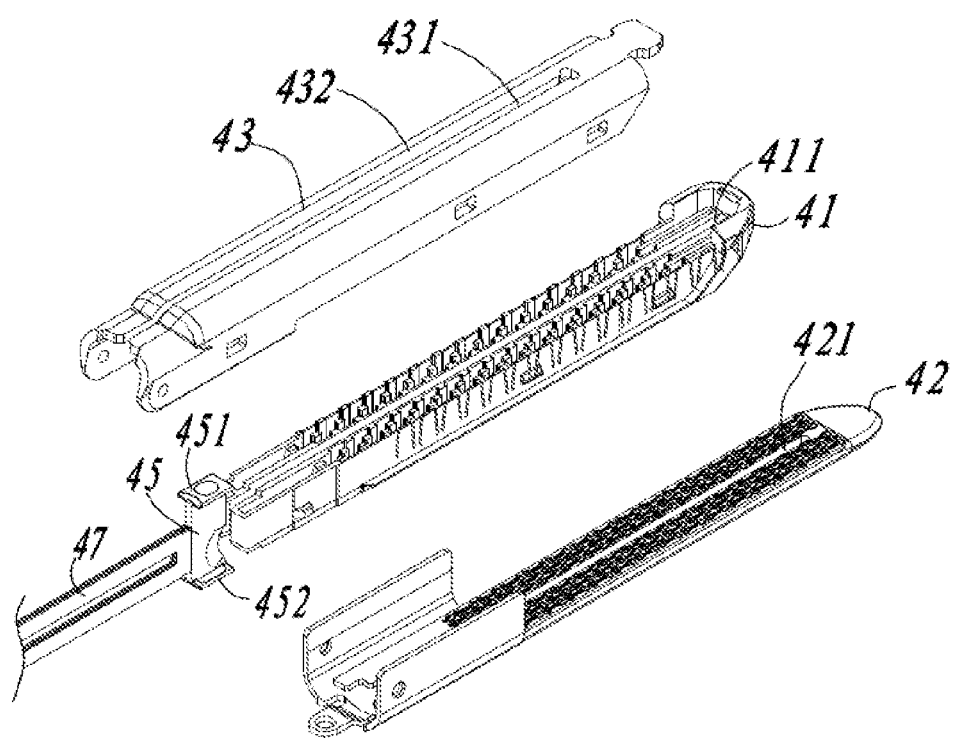
FIG. 3 is an exploded schematic structural view of a part of a stapler cartridge assembly according an embodiment of the present invention.

As shown in FIGS. 1-3, a medical stapler is used for applying multiple staples onto physiological tissues of a human body and cutting the corresponding physiological tissues by a cutter. The medical stapler includes an instrument main body 10, a rotation ring 20 matching with the instrument main body 10, and a firing handle 30 pivotably connected to the instrument main body 10.

The distal end of the instrument main body 10 is provided with a staple cartridge assembly 40, which includes a staple cartridge 41, an anvil 42, a staple cartridge bracket 43, a connector 44, an I-shaped cutter 45 and a joint 46 arranged at the distal end of the connector 44. By controlling the rotation direction and angle of the joint 46, an area defined by the staple cartridge 41 and the anvil 42 can rotate relative to the connector 44 to adapt to multi-angle cutting and stapling surgeries.

The staple cartridge bracket 43 defines a support passage in which the staple cartridge 41 is mounted and received. The staple cartridge bracket 43 is used for connecting the staple cartridge 41 to the connector 44.

In the present embodiment, the staple cartridge 41 and the anvil 42 is rotatably relative to each other. When they rotate to open status, the operated target physiological tissues can be placed between the staple cartridge 41 and the anvil 42. Then, by rotating the staple cartridge 41 and the anvil 42 to a closed status, the target physiological tissues between them are clamped to facilitate the following cutting and stapling operations.

When the medical stapler/staple cartridge assembly 40 is in an original status, the tail at the proximal end of the anvil 42 is applied with an external force to keep the anvil 42 and the staple cartridge 41 in an open status, and the I-shaped cutter 45 is located at the proximal end of the staple cartridge assembly 40.

When the medical stapler/staple cartridge assembly 40 is in the closed status, the anvil 42 and the staple cartridge 41 are driven by the I-shaped cutter 45 to be closed. The target physiological tissues can be clamped between the anvil 42 and the staple cartridge 41. The I-shaped cutter 45 moves a certain distance towards the distal end of the medical stapler/staple cartridge assembly 40 relative to the original status. But generally, the I-shaped cutter 45 is still located at the proximal end of the staple cartridge assembly 40.

When the medical stapler/staple cartridge assembly 40 is in a firing status, the anvil 42 and the staple cartridge 41 are kept to be closed to each other, and the I-shaped cutter 45 moves from the proximal end of the staple cartridge assembly 40 to the distal end thereof, cuts the clamped physiological tissues, and stops moving at the distal end of the staple cartridge assembly 40 when being limited.

As shown in FIG. 3, the staple cartridge bracket 43 includes a first abutting surface 432 which is away from the anvil 42 and cooperates with one end 451 of the I-shaped cutter 45, and the anvil 42 includes a second abutting surface which is at the back of the anvil surface and cooperates with the other end 452 of the I-shaped cutter 45.

The staple cartridge 41, the anvil 42 and the staple cartridge bracket 43 are provided with cutter receiving grooves 411, 421, 431 respectively to cooperate with the I-shaped cutter 45. The cutter receiving grooves 411, 421, 431 extend from the proximal ends of the staple cartridge 41, the anvil 42 and the staple cartridge bracket 43 to the distal ends thereof respectively. When the anvil 42 and the staple cartridge 41 are closed to each other, the cutter receiving grooves 411, 421, 431 cooperate with one another to form a passage along which the I-shaped cutter 45 can move from the proximal end of the staple cartridge assembly 40 to the distal end thereof or from the distal end thereof to the proximal end thereof.

The staple cartridge assembly 40 further includes a cutter push rod 47 connected to the proximal end of the I-shaped cutter 45. The cutter push rod 47 can drive the I-shaped cutter 45 to move from the proximal ends of the cutter receiving grooves 411, 421, 431 to the distal ends thereof or from the distal ends thereof to the proximal ends thereof. In this process, the cutter receiving grooves 411, 421, 431 provide a movement path and guide the I-shaped cutter 45 and the cutter push rod 47. When the area defined by the anvil 42 and the staple cartridge 41 rotates by a certain degree relative to the connector 44, the cutter push rod 47 bends for a certain degree accordingly, so that the I-shaped cutter 45 can smoothly move towards the distal end of the medical stapler.

Figure 4:
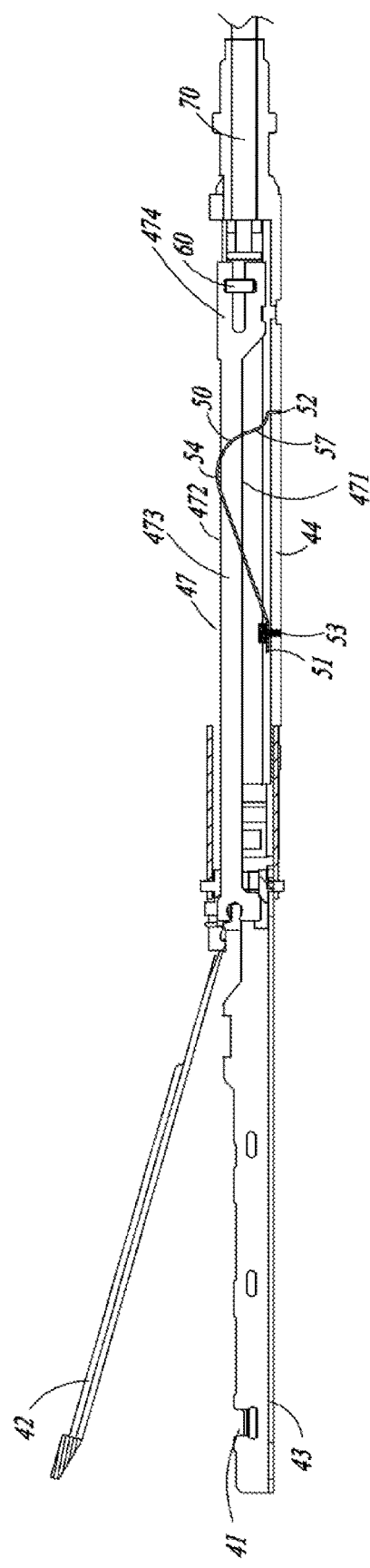
FIG. 4 is a schematic structural view of a stapler cartridge assembly in an original status according an embodiment of the present invention.
Figure 5:
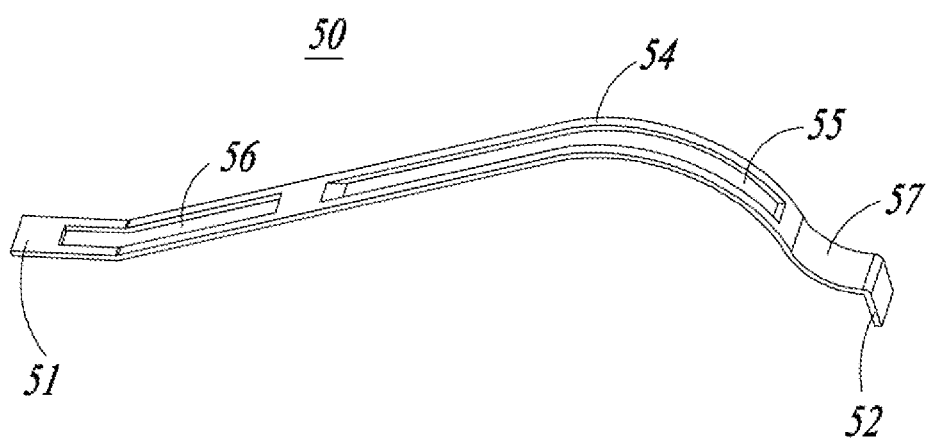
FIG. 5 is a schematic structural view of an elastic sheet when the stapler cartridge assembly is in an original status according an embodiment of the present invention.
Figure 6:
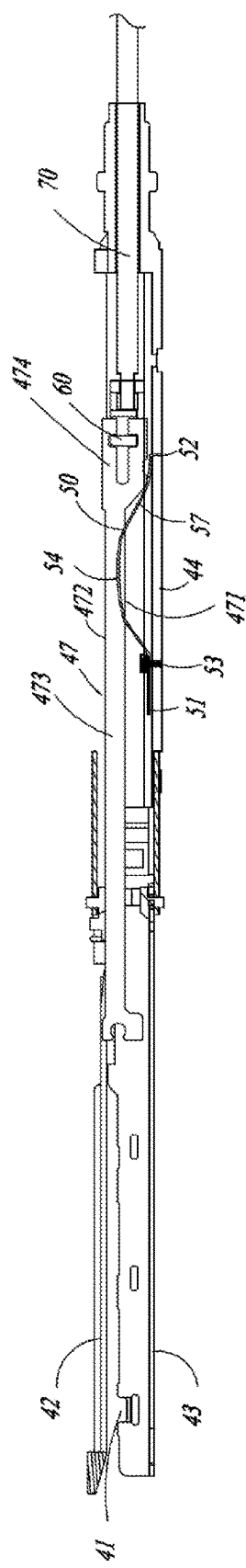
FIG. 6 is a schematic structural view of a firing process of a stapler cartridge assembly according an embodiment of the present invention.
Figure 7:
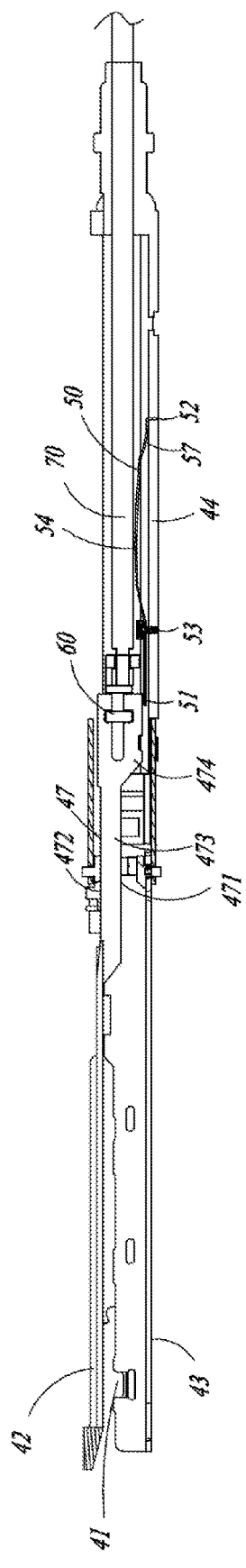
FIG. 7 is a schematic structural view when the firing process of a stapler cartridge assembly is finished according an embodiment of the present invention.

As shown in FIG. 4-8, the staple cartridge assembly 40 further includes an elastic sheet 50 having a first through groove 55. As shown in FIG. 3, the cutter push rod 47 is made of multiple sheets. As shown in FIG. 4-5, when the staple cartridge assembly 40 is in the original status or the closed status, a part of the cutter push rod 47 is located in the first through groove 55, which limits the detaching of the multiple sheets in a laminating direction of the multiple sheets. As shown in FIG. 6, in the firing process of the staple cartridge assembly 40, the cutter push rod 47 moves towards the distal end of the staple cartridge assembly 40 to press the elastic sheet 50. Then the elastic sheet 50 deforms and the cutter push rod 47 is gradually detached from the first through groove 55. As shown in FIG. 7, after the firing process of the staple cartridge assembly 40 is finished, the I-shaped cutter 45 stops at the distal end of the staple cartridge assembly 40 after being limited, and the cutter push rod 47 is completely detached from the first through groove 55.

In the present embodiment, the width of the first through groove 55 in the laminating direction of the multiple sheets is equal to or slightly greater than the thickness of the laminated multiple sheets, so that the first through groove 55 can better limit the multiple sheets forming the cutter push rod 47 from detaching from one another in the laminating direction of the multiple sheets.

In the present embodiment, as shown in FIG. 4-5, the elastic sheet 50 includes a first end 51 and a second end 52 connected to the connector 44 respectively; the first end 51 is located at a distal end of the second end 52; at least one of the first and second ends 51, 52 is movably connected to the connector 44. In the present embodiment, for example, the first end 51 is movably connected to the connector 44, and the second end 52 is fixedly connected to the connector 44. During the firing process of the staple cartridge assembly 40, the first end 51 moves towards the distal end of the staple cartridge assembly 40, but this case is not restrictive. In one example, the second end 52 is movably connected to the connector 44, and the first end 51 is fixedly connected to the connector 44. During the firing process of the staple cartridge assembly 40, the second end 52 moves towards the proximal end of the staple cartridge assembly 40. In another example, both the first and second ends 51, 52 are movably connected to the connector 44. During the firing process of the staple cartridge assembly 40, the first end 51 moves towards the distal end of the staple cartridge assembly 40, and the second end 52 moves towards the proximal end thereof.

In the present embodiment, as shown in FIG. 4-5, the first end 51 is movably connected to the connector 44. A second through groove 56 is provided between the first end 51 and the first through groove 55, and is movably connected to the connector 44 via a limiting member 53. The limiting member 53 is fixedly connected to the connector 44. When the staple cartridge assembly 40 is in the original status or the closed status or has finished its firing process, the second through groove 56 is stationary relative to the limiting member 53. During the firing process of the staple cartridge assembly 40, the limiting member 53 can slide in the second through groove 56, and the second through groove 56 moves towards the distal end of the staple cartridge assembly 40 relative to the limiting member 53. The limiting member 53 may be a limiting nail 53. The maximum diameter of a cap of the limiting member 53 is greater than a width of the second through groove 56 in the laminating direction of the multiple sheets to prevent the second through groove 56 from being detached from the limiting member 53.

In the present embodiment, the second end 52 is fixedly connected to the connector 44. The cutter push rod 47 includes a cutter push rod main body 473 and a tail end 474. The tail end 474 is located at the proximal end of the cutter push rod main body 473. The tail end 474 protrudes from the cutter push rod main body 473 in a direction along which the tail end 474 faces the second end 52. An abutting portion 57 is provided between the proximal end of the first through groove 55 and the second end 52. When the tail end 474 and the abutting portion 57 interfere with each other, the tail end 474 presses the elastic sheet 50 to deform the same.

In the present embodiment, the first and second through grooves 55, 56 cross the elastic sheet 50 in the thickness direction of the elastic sheet 50. The abutting portion 57 does not cross the elastic sheet 50, and is substantially a portion of the elastic sheet 50.

In the present embodiment, the proximal end of the cutter push rod 47 is connected with a firing rod 70 via a transmission block 60. The firing rod 70 controls the cutter push rod 47 to move towards the distal or proximal end of the staple cartridge assembly 40.

In the present embodiment, the work procedures of the staple cartridge assembly 40 are as below.

In the present embodiment, for example, the staple cartridge assembly 40 is horizontally placed, and the staple cartridge 41 is located below the anvil 42. Other positional terms refer to the above descriptions. In addition, in the present embodiment, for example, the elastic sheet 50 is arranged below the connector 44. The area below the connector 44 is an area adjacent to the staple cartridge 41, but this case is not restrictive. In other embodiments, the elastic sheet 50 may be arranged in other regions. The cutter push rod 47 includes a first end surface 471 formed by laminating the multiple sheets and a second end surface 472 away from the first end surface 471.

As shown in FIGS. 4-5, when the staple cartridge assembly 40 is in the original status or the closed status, a distance from the highest point 54 of the elastic sheet 50 to the first end surface 471 is greater than that from the highest point 54 to the second end surface 472. Preferably, the highest point 54 is higher than the second end surface 472. The tail end 474 of the cutter push rod 47 is away from the abutting portion 57 of the elastic sheet 50. The second through groove 56 is stationary relative to the limiting member 53. A part of the cutter push rod 47 is located in the first through groove 55, and the first through groove 55 restricts detaching of the multiple sheets from one another in a laminating direction of the multiple sheets.

As shown in FIG. 6, in the firing process of the staple cartridge assembly 40, the highest point 54 gradually departs from the second end surface 472 and gradually approaches the first end surface 471. When the cutter push rod 47 moves towards the distal end of the staple cartridge assembly 40, the tail end 474 of the cutter push rod 47 gradually approaches and presses the abutting portion 57 to deform the elastic sheet 50. The second through groove 56 moves towards the distal end of the staple cartridge assembly 40 relative to the limiting member 53. At this point, a part of the cutter push rod 47 is still located in the first through groove 55, and the first through groove 55 restricts detaching of the multiple sheets from one another in a laminating direction of the multiple sheets. When the highest point 54 gradually descends to a position near the first end surface 471, the tail end 474 of the cutter push rod 47 gradually detaches from the abutting portion 57, and the firing rod 70 gradually abuts against the elastic sheet 50. At this point, the cutter push rod 47, the transmission block 60 and the firing rod 70 can move above the elastic sheet 50, and continue to press the elastic sheet 50 until the cutter push rod 47 reaches the furthest end of the staple cartridge assembly 40.

Figure 8:
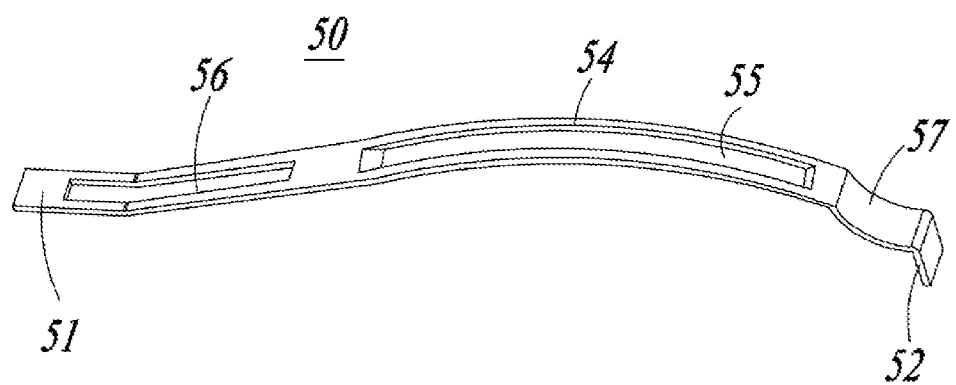
FIG. 8 is a schematic structural view of an elastic sheet when the firing process of a stapler cartridge assembly is finished according an embodiment of the present invention.

As shown in FIGS. 7-8, when the staple cartridge assembly 40 finishes the firing process, the elastic sheet 50 detaches from the cutter push rod 47. The tail end 474 of the cutter push rod 47 is away from the abutting portion 57 of the elastic sheet 50. The second through groove 56 is stationary relative to the limiting member 53. The elastic sheet 50 is located below the cutter push rod 47, and the transmission block 60 and the firing rod 70, so that when the cutter push rod 47 approaches the proximal end of the staple cartridge assembly 40, the cutter push rod 47, the transmission block 60 and the firing rod 70 can move above the elastic sheet 50. As shown in FIG. 4, the elastic sheet 50 is located at a midway between the proximal and distal ends of the connector 44. The midway is a position where when the cutter push rod 47 bends for an angle, the multiple sheets can most easily detach from one another.

In the present embodiment, when the area defined by the anvil 42 and the staple cartridge 41 rotates by a certain degree relative to the connector 44, the cutter push rod 47 bends for a certain degree accordingly. The distal end of the cutter push rod 47 is clamped between the first and second cutter receiving grooves 411, 421, and the proximal end thereof is clamped in the first through groove 55. When the cutter push rod 47 pushes the I-shaped cutter 45 to forward, due to limiting of the proximal end of the cutter push rod 47 by the first through groove 55, the multiple sheets forming the cutter push rod 47 do not detach from one another, so that the cutter push rod 47 can stably push the I-shaped cutter 45 to forward.

To sum up, in the present invention, by limiting the multiple sheets using the first through groove 55 in the elastic sheet 50, the multiple sheets do not detach from one another in their laminating direction; the cutter push rod 47 can smoothly move towards the distal or proximal ends of the staple cartridge assembly 40 through deformation of the elastic sheet 50, and blocking of the cutter push rod 47 by the elastic sheet 50 is avoided.

It should be understood that although the description is described according to the above embodiments, each embodiment may not only include one independent technical solution. The presentation manner of the description is only for the sake of clarity. Those skilled in the art should take the description as an integral part. The technical solutions of the respective embodiments may be combined properly to form other embodiments understandable by those skilled in the art.

The above detailed description only illustrates the feasible embodiments of the present invention, and is not intended to limit the protection scope of the present invention. Equivalent embodiments or modifications within the scope and spirit of the present invention shall be embraced by the protection scope of the present invention.

The invention claimed is:

1. A medical stapler, comprising:
a staple cartridge assembly comprising a connector, a cutter push rod, a cutter and an elastic sheet, the cutter push rod connecting to a proximal end of the cutter, the elastic sheet having a first through groove and the cutter push rod being formed by laminating multiple sheets, wherein when the staple cartridge assembly is in a closed status with respect to an anvil, part of the cutter push rod is located in the first through groove, and the first through groove restricts detaching of the multiple sheets in a laminating direction of the multiple sheets; in a firing process of the staple cartridge assembly, the cutter push rod moves towards a distal end of the staple cartridge assembly to press the elastic sheet, such that the elastic sheet deforms and the cutter push rod is gradually detached from the first through groove; after the firing of the staple cartridge assembly is finished, the cutter push rod is detached from the first through groove; and
a firing rod which abuts against the elastic sheet after the firing of the medical stapler is finished.

2. The medical stapler of claim 1, wherein the cutter push rod includes a first end surface formed by laminating the multiple sheets and a second end surface away from the first end surface; when the staple cartridge assembly is in the closed status, a distance from a point of the elastic sheet to the first end surface is greater than that from the point to the second end surface; in the firing process of the staple cartridge assembly, the point gradually departs from the second end surface and gradually approaches the first end surface; after the firing of the staple cartridge assembly is finished, the elastic sheet is detached from the cutter push rod.

3. The medical stapler of claim 1, wherein the elastic sheet includes a first end and a second end that are movably connected to the connector; the first end is located at a distal end of the second end; during the firing process of the staple cartridge assembly, the first end moves towards the distal end of the staple cartridge assembly, and the second end moves towards the proximal end thereof.

4. The medical stapler of claim 1, wherein the elastic sheet includes a first end movably connected to the connector and a second end fixedly connected to the connector; the first end is located at a distal end of the second end; during the firing process of the staple cartridge assembly, the first end moves towards the distal end of the staple cartridge assembly.

5. The medical stapler of claim 4, wherein the staple cartridge assembly further includes a limiting member; a second through groove is provided between the first end and the first through groove, and is movably connected to the connector via the limiting member; when the staple cartridge assembly is in the closed status, the second through groove is stationary relative to the limiting member; during the firing process of the staple cartridge assembly, the limiting member can slide in the second through groove, and the second through groove moves towards the distal end of the staple cartridge assembly relative to the limiting member.

6. The medical stapler of claim 5, wherein the limiting member is a limiting nail fixedly connected to the connector.

7. The medical stapler of claim 4, wherein the cutter push rod includes a cutter push rod main body and a tail end; the tail end is located at the proximal end of the cutter push rod main body; an abutting portion is provided between the proximal end of the first through groove and the second end; when the cutter push rod moves towards the distal end of the staple cartridge assembly, the tail end presses the abutting portion to deform the elastic sheet.

8. The medical stapler of claim 1, wherein the elastic sheet is located at a midway between the proximal and distal ends of the connector.

* * * * *